United States Patent [19]

Gottschalk et al.

[11] Patent Number: 5,306,633

[45] Date of Patent: Apr. 26, 1994

[54] BACTERIAL XYLANASE, METHOD FOR ITS PRODUCTION, BACTERIA PRODUCING A XYLANASE, DNA FRAGMENT ENCODING A XYLANASE, PLASMID CONTAINING THE DNA FRAGMENT, BAKING AGENTS CONTAINING A XYLANASE, AND METHOD FOR PRODUCING BREAD AND BAKED GOODS USING THE XYLANASE

[75] Inventors: Michael Gottschalk, Ober-Ramstadt; Erwin Schuster, Bensheim-Auerbach; Bruno Sprössler, Rossdorf, all of Fed. Rep. of Germany

[73] Assignee: Rohm GmbH Chemische Fabrik, Darmstadt, Fed. Rep. of Germany

[21] Appl. No.: 104,445

[22] Filed: Aug. 10, 1993

[30] Foreign Application Priority Data

Aug. 11, 1992 [DE]  Fed. Rep. of Germany ....... 4226528

[51] Int. Cl.$^5$ .......................... A23L 1/28; C12N 9/24; C12N 9/26; C07H 21/04

[52] U.S. Cl. .................................. 435/200; 435/69.1; 435/201; 435/209; 435/252.3; 435/252.31; 536/22.1; 536/23.2; 536/23.7; 426/653

[58] Field of Search ........... 435/201, 200, 209, 252.3, 435/252.31, 69.1; 536/22.1, 23.2, 23.7; 426/653

[56] References Cited

PUBLICATIONS

Paice et al. *Arch. Microbiol.* 144:201–206 (1986).

*Primary Examiner*—Charles L. Patterson, Jr.
*Assistant Examiner*—Hyosuk Kim
*Attorney, Agent, or Firm*—Oblon, Spivak, McClelland, Maier & Neustadt

[57] ABSTRACT

A novel xylanase, obtained from *Bacillus subtilis* strains, is provided which improves the consistency and increases the volume of bread and baked goods containing it. *B. subtilis* DSM 7147 containing the plasmid pIK 91 produces the xylanase. Genetic engineering insertion of the gene encoding the xylanase in the plasmid pUB110 is described.

3 Claims, No Drawings

BACTERIAL XYLANASE, METHOD FOR ITS PRODUCTION, BACTERIA PRODUCING A XYLANASE, DNA FRAGMENT ENCODING A XYLANASE, PLASMID CONTAINING THE DNA FRAGMENT, BAKING AGENTS CONTAINING A XYLANASE, AND METHOD FOR PRODUCING BREAD AND BAKED GOODS USING THE XYLANASE

BACKGROUND OF THE INVENTION

1. Field of the Invention

The invention provides a new bacterial xylanase, a method for its production as well as a bacteria strain suitable for producing it. The invention also provides a plasmid containing a gene encoding the bacterial xylanase. The invention also provides a baking agent and a method for producing bread and baked goods using the new xylanase, wherein the xylanase increases the volume and improves the consistency of the dough.

2. Background of the Invention

In the production of yeast raised bread and baked goods, particularly in the production of white bread and rolls, it is desirable to obtain a high baking volume in the baked product. The baking volume depends on a number of factors, most of which are dependent on the properties of the flour used to form the dough. However, even when the best types of flour are used, it is still desirable to increase the baking volume. Accordingly, baking additives which increase the baking volume of bread and baked goods are desirable. Besides increasing the baking volume of baked goods made with high quality flour, it is also desirable to increase the baking volume of baked goods made with inferior types of flour.

Previous baking additives which have been found to increase the baking volume of baked goods include emulsifiers, oxidizers, reduction agents, yeast activators, enzymes such as amylases, proteases and pentosanases, pH stabilizers, mucins and fats.

For example, Kosmina ("Biochemie der Brotherstellung" [Biochemistry of Bread Production], Leipzig 1975, p. 324) disclose that although the presence of so-called "residual fractions", also referred to as mucins or tailings, in wheat flour increases the water absorption capacity of dough made from it, they also reduce the baking volume and worsen the porosity of the bread. These disadvantages can be eliminated by pretreating the "residual fractions" with a cellulase preparation made from *Trichoderma viride* ("MEICELASE", commercially available from Meiji).

The baking volume of dough can also be increased by adding enzymes, particularly amylases and/or proteases, to the dough, particularly when the flour used to form the dough has too low an enzyme content of its own. Unfortunately, this increases the baking volume of the dough only slightly. The incorporation of baking emulsifiers, in addition to these enzymes, results in a slight volume increase. Other additives, such as yeast activators, oxidizers and reduction agents, further increase the volume.

G. Reed ("Enzymes in Food Processing," Academic Press: New York & London, 1966, p. 253) disclose that the presence of insoluble pentosanes in flour reduces the baking volume of baked goods. To improve the baking volume, pentosanases, which reduce pentosan, were added to the bread dough. Unfortunately, the effects observed were only slight, and could not be reproduced consistently.

Rotsch ("Brot und Gebäck" [Bread and Pastry], 1966, p. 91) found that the effect of adding pentosanases to the bread dough could not be augmented by simultaneously adding baking emulsifiers. Thus, the effect is not additive when emulsifiers and pentosanases are used simultaneously.

Pentosanases have also been suggested as preservatives for baked goods. Cooke and Johnson (DT-AS 1,767,119) demonstrated that pentosanases were better preservatives than baking emulsifiers.

Pentosanases have also been added to rye flours which have a high pentosane-starch ratio. When this ratio is too high, the dough made with such flours has too high a viscosity, due to subsequent swelling of the rye pentosanes, and results in a baked product where the center is torn away from the crust. By adding pentosanases, the pentosanes can be reduced and the dough viscosity can be lowered accordingly. Consequently, the center does not tear away from the crust when the dough is baked.

When pentosanases are added to processed flours which have a balanced pentosane-starch ratio, the viscosity of the dough is reduced to such a degree that flat bread is formed. The addition of pentosanases is therefore advantageous only in exceptional cases, whereas it is disadvantageous in the majority of cases.

DE-A 40 17 150 describes the production of xylanase, a pentosanases, in cultures of fungus and bacteria containing beta-methyl xyloside. The properties of the xylanases formed are greatly dependent on the microorganism from which they are produced.

Baking additives according to this description are supplied under the brand name "OLYMPIAL" by Boehringer Ingelheim Backmittel GmbH, Bingen, Germany, under the brand name "ORKAN" by Ratjen-Backmittel, Flintbek, Germany, or under the brand name "S 500" by Puratos S. A., Groot-Bijgaarden, Belgium. To date, nothing has been published about the characteristics of this enzyme mixture and how it is obtained. Along with the amylase activity, a xylanase activity can also be detected in the enzyme mixture. The scope of properties of this enzyme is consistent with those of fungal xylanases which belong to the enzyme group of pentosanases. However, the effect on the baking volume of baked goods produced by the enzyme mixture is far superior to that produced by known xylanases which all originated from fungi.

Although various other baking enzymes are available which degrade cellulose, their effect remains far behind that of the xylanase mentioned above.

SUMMARY OF THE INVENTION

Accordingly, one object of the present invention is to provide a novel baking enzyme which has an effect equivalent to that of the baking aid mentioned above.

A second object of the present invention is to provide a method for producing this novel baking enzyme.

A third object is to provide a method for producing yeast baked goods with greater volume, using wheat flour containing the baking enzyme.

The inventors have now found that novel xylanases with the desired properties can be obtained from certain bacteria cultures.

BRIEF DESCRIPTION OF THE APPENDICES

SEQ ID NO:1 contains the entire DNA sequence cloned from RH1221. Starting with nucleotide 506, there is an open reading frame encoding 213 amino acids.

SEQ ID NO:2 contains the DNA sequence of the gene encoding the *B. subtilis* RH 1221 xylanase. This gene is contained in the plasmid of *B. subtilis* RH 1330 pIK 91.

SEQ ID NO:3 contains the amino acid sequence of the xylanase produced from *B. subtilis* RH 1221.

DETAILED DESCRIPTION OF THE PREFERRED EMBODIMENTS

The present inventors have now found a novel bacterial xylanase, which can be produced by expression of the gene pursuant to SEQ ID NO:2, which, when incorporated into dough, increases the baking volume of baked goods produced from the dough.

The present inventors believe that this novel xylanase partially reduces mucins in the flour, thereby increasing the swelling of the dough; it is noteworthy that the reduction of the mucins does not result in a dissolution of the insoluble xylan particles. Whatever the effect, the xylanase influences the viscosity of dough containing it. In particular, the dough becomes fluffy and soft, which appears to be causally connected with the increase in baking volume. However, since the viscosity behavior and the baking volume of yeast doughs are dependent on a variety of factors, the effect of the enzyme of the present invention cannot be definitively characterized by this trait.

However, the xylanase of the present invention can be differentiated from known xylanases on the basis of its amino acid sequence. In particular, the xylanase of the present invention differs from a previously known *B. subtilis* xylanase (Paice et al, Arch. Microbiol. (1986), 144: 201-206) in 45 positions of the nucleotide sequence and in 10 positions of the amino acid sequence. Of the ten different amino acids, six are within the sequence of the mature protein which is formed after cleavage of a 28 amino acid long signal peptide. Thus, the mature protein begins at position 29 in SEQ ID NO: 3 and contains 185 amino acids. Accordingly, the xylanase of the present invention has not previously been described. The present inventors believe that the unique baking effect of the new xylanase is due to the differences in the amino acid sequence, individually or in combination.

When the xylanase according to the present invention is added to dough made from wheat flour, the baking volume of the yeast baked goods produced increases 20 to 30 fold, in some cases even higher. This effect is achieved with all types of wheat flours—an effect which has not previously been observed with other baking agents—even when the dough was optimized by additions of amylases, proteases and emulsifiers. Furthermore, the dough consistency is improved and the formation of fluffy dough is achieved. The porosity of the baked goods is also improved.

The xylanase of the present invention can be used in the production of all yeast baked goods made from dough based on wheat flour. Preferably, the xylanase of the present invention is used in the production of white breads and rolls. However, it can also be advantageously used in the production of French rolls, yeast cakes and yeast pastries.

The xylanase according to the invention can be obtained from a variety of bacteria. Using normal selection methods, microorganisms which produce this xylanase at high activity and specificity can be selected from among microorganisms which produce other xylanases. Suitable bacteria which produce the xylanase according to the invention can be identified using standard procedures by analyzing for the presence of the corresponding gene in the producing bacterium. As an ancillary measure, transcription of the gene encoding the xylanase into the corresponding peptide sequence can be used to identify the xylanase itself.

Suitable bacteria strains which form the novel xylanase according to the present invention are found in the genus Bacillus and include the species *B. subtilis, B. amyloliquefacens, B. natto, B. mesentericus, B. licheniformis, B. stearothermophilus, B. coagulans, B. pumilus, B. megaterium, B. circulans* and *B. firmus*. Although it is possible to obtain the desired xylanase from the culture filtrate of the aforementioned bacteria strains, the productivities of these strain are low and do not meet the requirements established for large-scale industrial production. Therefore, it is preferable to obtain the xylanase according to the present invention using recombinant DNA techniques.

That is, it is preferred to transfer the definitive genetic information for formation of the xylanase according to the present invention from one of the microorganisms mentioned above to other microorganisms which are easy to culture and from which the enzyme can be easily purified. Transformed microorganisms have significantly increased productivity of the xylanase of the present invention.

A suitable bacteria strain transformed in this way and designationed *B. subtilis* RH 1330 pIK 91, was filed with the Deutsche Sammlung von Mikroorganismen und Zellkulturen GmbH [German Collection of microorganisms and Cell Cultures, Inc.] in Braunschweig under Accession No. DSM 7147, pursuant to the provisions of the Budapest Convention. However, the production of the xylanase according to the present invention is not limited to the use of this specific strain.

By testing other microorganisms which produce xylanase, and comparing the xylanase against the present invention's xylanase, other suitable strains can be found. The genome obtained from these strains can be transferred to a suitable plasmid, using genetic engineering methods, and can then be easily introduced into bacteria strains which are easy to cultivate and represent no toxicology problems (See, Sambrook et al., In "Molecular Cloning: A laboratory manual:, 2 ed., Vols. 1-3, Cold Spring Harbor Laboratory: N.Y., 1989; incorporated herein by reference). These recombinant bacteria can then be screened for high productivity of the xylanase. Recombinant bacteria with high productivity of xylanase are suitably cultured in culture broths or extracts. The xylanase can be obtained from the cultures by conventional means such as by separation of the insoluble cell and nutrient components, concentration of the filtrate by means of ultrafiltration, precipitation with salts or organic liquids, or drying by spraying, fluidized drying or lyophilization. The xylanase is preferably produced and used in granulate or powder form. As compared with cultures of fungi, the cultures of bacteria according to the invention have the advantage that they require fermentation times of only one to two days, whereas culturing times for fungi range from three to five days.

The xylanase according to the invention, has a molecular weight of about 20,000 Daltons, whereas the majority of known fungal xylanases have higher molecular weights. These known fungal xylanases do not increase the baking volume of yeast baked goods to the same extent as the xylanase of the present invention.

The pH optimum of the bacterial xylanase of the present invention is about pH 6.0, and therefore corresponds to the typical pH of dough. In contrast, fungal xylanases have a pH optimum at pH 4.5–5.0.

The volume efficacy of xylanases according to the present invention is dependent on the amount of xylanase added to the dough. At low dosage, the volume increase correlates with the amount of enzyme used, but after a certain enzyme amount, a maximum volume increase is reached; this volume can not be increased by adding more xylanase. The baking volume can decrease again if the dough contains an overdose of the enzyme. The inventors believe the decrease is due to the continuing reduction of the xylan. The surprising efficacy of the xylanase according to the invention presumably is due to the fact that in a suitable dosage, it results in relatively rapid digestion of the previously insoluble wheat mucins, which were only able to swell to a limited extent, so that they become particles which are still not dissolved, but have a great capacity for swelling, and that further reduction to dissolved hydrolysis products proceeds slowly. In contrast to this, the majority of known xylanases continuously reduces the wheat mucins to soluble end products, so that the intermediate step at a high level of swelling does not occur.

The xylanase according to the invention can be used in a mixture with other baking ingredients. The addition of other baking additives makes it easier to control the dosage of xylanase and makes it easier to mix the xylanase uniformly intio the dough. Suitable baking agents include any conventional ingredients useful in the production of yeast baked goods. However, it is not practical to mix the xylanase with liquid starting substances, such as milk or water, or with yeast. Preferred mixture components are flour, sugar, salt, fats and baking emulsifiers. Suitable baking emulsifiers include those frequently used in the production of yeast baked goods to improve the consistency of the finished product. Suitable examples include monoglycerides, diglycerides and triglycerides of fatty acids, lecithin and diacetyl tartaric acid. The preferred baking agents according to the invention contain the xylanase blended with such baking emulsifiers. The baking agent is suitably produced by uniform mixing of the xylanase with the other ingredients, for example in a mixing drum or in a kneader.

Other baking enzymes, such as amylases and proteases, can also be included into the baking agents of the present invention. The activity of xylanase in the presence of xylan is expressed in xylanase units (UXyl), where 1 UXyl corresponds to the amount of enzyme which releases reducing groups with an equivalent value of 1 $\mu$Mol xylose per minute from xylan at 30° C., under standard conditions. The xylanase activity of the baking agent of the present invention is suitably between 0.1 and 10 UXyl/g.

For the production of white bread and rolls, the baking agent is generally dosaged in such a way that 200 to 20,000 UXyl, preferably 200 and 2,000 UXyl, are used per 100 kg wheat flour. In contrast, when fungal xylanases are used, the dosage is higher, usually between 1000 and 10,000 UXyl.

The xylanase according to the present invention can be stored at room temperature for several years without significant loss in activity. Baking agent formulations comprising the xylanase according to the present invention in addition to other ingredients which do not harm the activity of the xylanase, such as proteases, have a similar shelf life. Suitably, the water content of baking agent formulation is below 5%, and below 1% when diacetyl tartartic acid emulsifiers are present.

Yeast baked goods from wheat flour, yeast, water or milk, fat, salt, sugar and other conventional additives and flavorings can be produced by conventional procedures. The baking agents according to the present invention can be added to the dough without requiring any change in the usual baking methods. The conventional resting time required for yeast dough is sufficient to allow the xylanase to act.

Having generally described this invention, a further understanding can be obtained by reference to certain specific examples which are provided herein for purposes of illustration only and are not intended to be limiting unless otherwise specified.

EXAMPLES

Example 1. Screening of Bacillus Strains

*B. subtilis* bacteria strains obtained from soil or water samples or purchased from public strain collections were first cultured on an indicator nutrient base composed of nutrient agar and an additive of 1% microfine xylan, at 37° C., for 24 to 48 hours. Strains which form xylanase were recognized by the hydrolysis halos around the individual colonies. Of 367 bacteria strains tested, approximately 229 were able to reduce xylan. These were transferred to slanted agar tubes and served as strain cultures for the tests described below.

The strains were cultured in a sterile, aqueous nutrient solution containing 6% soybean flour and 4% xylose at pH 6.0–6.2, at 37° C., in shaker flasks, for 24 hours. After separation of the solids, the xylanase activity was determined in the aqueous solution at pH 6.0, which is the pH optimum for bacterial xylanase. For this purpose, a mixture of 0.75 mL xylan solution (Nutritional Biochemical Corporation, NBC, 0.5% in 0.04 M Na acetate buffer pH 6.0) and 0.25 mL enzyme solution (in suitable dilution) was incubated at 30° C. for 15 minutes. The resulting reducing groups were then determined using the method of Somogyi and Nelson (Methods in Enzymology, Academic Press: New York, London, 1966, Vol. VIII. p. 7). The activity 1 UXyl corresponds to the amount of enzyme which releases reducing groups equivalent to 1 $\mu$Mol xylose per minute from xylan at 30° C., under standard conditions.

The xylanase amount was read off from a calibration curve which was determined with the solution of pure xylose. The enzyme solutions were diluted in such a way that the extinction differences between the main value and the blind value did not lie above 0.25 extinction units.

Eighty strains with a xylanase activity of at least 2 UXyl/mL culture solution were found. In a second selection process, the culture top fractions of these strains were tested in the baking test, with regard to their volume increasing effect. In this process, 8 strains which produce the xylanase according to the invention in an amount that can be exploited were found, while the other 72 strains formed a xylanase which did not or only slightly increased the volume, or actually reduced the volume.

In the following table, the xylanase activity in the top culture fraction and the volume increase in the baking test are listed for six of the strains mentioned (See Example 8).

| Strain designation | Xylanase activity | Volume increase in baking test |
| --- | --- | --- |
| RH 1225 | 3.5 | +45% |
| RH 1223 | 4.0 | +36% |
| RH 1221 | 6.0 | +31% |
| RH 1242 | 2.4 | +37% |
| RH 1205 | 11.3 | +8% |
| RH 1114 | 8.0 | −10% |

One of the strains with high xylanase activity which proceeded from Example 3, which can be assigned to the species *Bacillus subtilis* and is characterized by a good volume increase in the baking test, was selected for the production of the enzyme in the laboratory fermenter, and received the designation RH 1221.

As is usual in enzyme development, a variant which has lost the capacity for sporulation and protease formation was selected from the wild type strain. This strain, which has been adapted to the needs of production, was used for enzyme production in the following Example 4.

Example 2. Production of the Bacteria Xylanase in the Laboratory Fermenter

For preparation of a nutrient solution, the following are used per liter:

```
60 g soybean flour
40 g xylose
13 g ammonium hydrogen phosphate
0.5 g magnesium sulfate × 7 H20
5 g calcium carbonate
tap water to 1000 g.
```

All of the nutrient ingredients except xylose were first mixed together. The pH was adjusted to 6.0–6.2. The solution Was sterilized in a fermenter at 121° C. for 30 minutes under pressure. The xylose solution was sterilized separately and was added after it had cooled.

First, a preliminary culture was mixed. For this purpose, 400 mL of the above nutrient solution were inoculated with a slanted agar culture according to Example 3, using a inoculation eye, and incubated for 10 hours.

The laboratory fermenter was inoculated with the content of this preliminary culture, under sterile conditions. The laboratory fermenter was then filled with 8 L of the nutrient solution described above. After inoculation with the preliminary culture, the solution was stirred at 700 rpm and aerated at 52 L air per hour and liter. After an incubation period of 20 hours at 37° C., the solution which contains the enzyme was separated by centrifugation or filtration, and examined for xylanase activity.

The proteinase activity was also determined since it also effects the dough softening during the baking test. The proteinase activity should therefore be as low as possible.

In the clarified fermentation broth, a xylanase activity of 30 UXyl/g was measured. The broth was centrifuged, concentrated by means of ultrafiltration, and finally lyophilized. A powdered enzyme preparation with an activity of 1,500 UXyl/g was obtained. The xylanase activity was determined as in Example 3.

Example 3. Obtaining a Recombinant *Bacillus subtilis* Strain

Chromosomal DNA was prepared from the *B. subtilis* strain with the designation RH 1321 according to the Marmur method (J. Mol. Biol. (1961) 3:268) and partially cleaved with the restriction enzyme Sau3A. The resulting DNA fragment had a size distribution with a maximum at about 3000 to 5000 base pairs.

The commercially available plasmid pUB110 was completely cleaved with the restriction enzyme BamHI and a ligation mixture was prepared with the aforementioned DNA fragments.

This mixture was transformed into a xylase-negative *B. subtilis* mutant, which had been developed from a commercially available strain with the designation *B. subtilis* Marburg (Mb) 168 H1, by mutation and selection. The transformation was carried out according to the Spizizen method (Proc. Natl. Acad. Sci. (1958) 44:1072). Cells which had taken up plasmid DNA were selected by means of the antibiotic kanamycin, because a kanamycin resistance gene was contained in the pUB110 portion of the newly combined plasmids. For selection, the transformed cells were individually placed on a nutrient base containing kanamycin. Xylanase formation was determined by observing which plates turned cloudy due to additional xylan content.

Among approximately 20,000 colonies which had become kanamycin resistant by inclusion of the plasmid, one colony was found which indicated the formation of xylanase with a small hydrolysis halo. The colony was isolated, multiplied and scattered over the kanamycin/xylan nutrient base again. The subsequent colonies all demonstrated a xylan hydrolysis halo.

Example 4. Sequencing of the Xylanase gene from RH 1221

From the clone obtained in Example 5, a plasmid of about 6 kBp was isolated and designated pIK91. The DNA inserted into the initial plasmid pUB110, originating from RH 1221, was sequenced according to the Sanger method. The sequence determined is reproduced in the appendix to the specification, as SEQ ID NO:1. In the 1413 base pairs, an open reading frame (a sequence encoding a protein) was found for 213 amino acids, which is indicated in SEQ ID NO:2.

Example 5. Testing of the Expressed Xylanase in the Baking Test

To test the bacteria xylanase cloned in *B. subtilis* Mb 168 H1 according to Example 4, shaker flask cultures were used and the top culture fraction was compared with that of the donor strain RH 1221 and that of the host strain Mb 168 H1. For this purpose, preliminary cultures of 5 mL Standard I bouillon in 100 mL Erlenmeyer flasks were inoculated with an inoculation eye without a baffle plate, and incubated at 200 rpm and 37° C. in a round shaker with a shaking diameter of 50 mm. In the case of the strain recombined according to the invention, *B. Subtilis* Mb 168 H1, the preliminary culture additionally contained 10 μg/mL kanamycin. From the preliminary cultures, 15 mL main culture medium (4% lactose, 6% soybean flour, 1.3% $(NH_4)_2HPO_4$, 0.5% $CaCO_3$, 0.05%, $MgSO_4 \times 7\ H_2O$ in tap water, pH 6.5) were inoculated with 150 μL preliminary culture in 100 mL Erlenmeyer flasks with a baffle plate in each instance, and incubated at 200 rpm and 37° C. in a round shaker with a shaking diameter of 50 mm. Subsequently, the cells were centrifuged off and the top culture fraction was analyzed. The following results were obtained:

| Strain | UXyl pH 6 | Baking Test |
|---|---|---|
| Donor RH 1221 | 10.6 | +29% |
| Host Mg 168 H1 | 0.0 | 0% |
| Recombin. Mb 168 H1 pIK91 | 2.8 | +31% |

*B. subtilis* Mb 168 H1 pIK91 produces a xylanase with baking activity which is equivalent in effect to the bacteria xylanase from the strain RH 1221 but which is produced in lower yield.

Example 6. Increase in Xylanase Productivity

The productivity of the strain *B. subtilis* Mb 168 H1 pIK91 is not sufficient for economically efficient production of the bacteria xylanase. To obtain a strain with greater productivity, a number of highly productive xylanase strains of the species *B. subtilis* were transformed with the plasmid pKI91 according to the Chang and Cohen method (Molec. Gen. Genet. (1979) 168, 111-115). The transformants Which contained the plasmid pIK 91 were tested for xylanase productivity as described in Example 5. For a further comparison, a technical production strain for alpha amylase, with the designation BS22/17, was transformed and cultivated and analyzed in the same manner.

In the top culture fractions, the following xylanase activities were found:

| Strain | (UXyl/g) | Activity of plasmid-free host strain (UXyl/g) |
|---|---|---|
| RH 1321 pIK 91 | 15.2 | 10.2 |
| RH 1308 pIK 91 | 19.5 | 6.0 |
| RH 1330 pIK 91 | 57.8 | 8.5 |
| BS 22/17 pIK91 | 2.8 | 3.0 |

These results demonstrate that the productivity of the recombinant strain cannot be predicted from the productivity of the starting strain. Strains with high initial productivity were clearly inferior to a recombinant strain of lesser initial productivity, after recombination.

Example 7. Bacteria Xylanase Production by Means of the Recombinant Strain *B. subtilis* RH 1330 pIK 91

7.1 Maintaining the strain: the strain culture was overinoculated on slanted tubes every week, incubated at 37° C. for 24 hours and stored at 4° C. Composition of the slant tube nutrient base
NZ-amine, casein, enzymatically hydrolyzed (SIGMA C 0626) 10 g/L
Yeast extract (SIGMA C 0626) 5 g/L
Cooking salt 8 g/L
Agar 10 g/L
distilled water
pH 7.2 with NaOH; sterilization 30 minutes at 121° C. After cooling to 45° C., 10 mg/L kanamycin was added and the mixture was immediately poured into Petri dishes.

7.2 Preliminary culture: 1 L Erlenmeyer flasks with baffle plates are filled with 100 mL nutrient solution with the following composition:
NZ-amine, casein, enzymatically hydrolyzed (SIGMA C 0626) 10 g/L
Yeast extract (SIGMA C 0626) 5 g/L
Cooking salt 8 g/L
pH 7.2 with NaOH; sterilization 30 minutes at 121° C. After cooling to 45° C., 10 mg/L kanamycin was added. The nutrient solution was inoculated with the strain culture 7.1 and shaken at 37° C for 16 hours.

7.3 Preliminary fermenter: 8 L of the nutrient solution used in 7.2 was inoculated with 500 mL of the preliminary culture 7.2. Culture conditions: 37° C., aeration 4.8 L/min, stirring at 700 rpm, 8 hours.

7.4 Main fermenter: 100 L of a nutrient solution of

| Soybean flour | 80 g/L |
|---|---|
| Lactose | 60 g/L |
| Diammonium hydrogen phosphate | 10 g/L |
| Magnesium sulfate × 7 H$_2$O | 0.5 g/L |
| Calcium carbonate | 5 g/L | pH = 5.8–6.0, sterilization 30 minutes at 121° C.

At 37° C., inoculation with 5 L of the prefermenter solution 7.3 takes place. Culture conditions: 37° C., aeration 60 L/min, stirring at 600 rpm, 30 hours. The culture broth was subsequently clarified by filtration and separation. The filtrate, i.e. the top fraction, was concentrated by ultrafiltration and lyophilized. Approximately 800 g lyophilizate with an activity of 15,000 UXyl/g was obtained.

Example 8. Baking Test

A dough was prepared from 100 parts by weight flour, 2 parts by weight salt, 3 parts by weight baking yeast, 58–60 parts by weight water and 40–50 ppm (with reference to the dough weight) ascorbic acid, in a spiral kneader (manufactured by Kemper), at 2–3 min at low Level I and 3–4 min at higher Level II. The amounts of enzyme indicated in the Table were added to the water before the start of the kneading process. For a comparison with the bacteria xylanase produced according to Example 7, the enzyme mixture containing xylanase which was mentioned initially was used. The dough temperature was 25°–27° C. After the dough was allowed to rest for 20 min, the dough was divided into pieces of 350 g each and shaped for the production of free-form white bread, allowed to rise at 32° C. and 80% relative humidity for 65 min, and baked at 230° C. for 30 minutes.

In the following table, the bread volume is indicated for different amounts of enzyme.

| without enzyme | 1264–1296 ccm |
|---|---|
| Commercially available baking enzyme: | |
| 1500 UXyl/100 kg flour | 1304 ccm |
| 1000 UXyl/100 kg flour | 1304 ccm |
| 4500 UXyl/100 kg flour | 1372 ccm |
| Bacteria xylanase obtained in Example 7: | |
| 1500 UXyl/100 kg flour | 1392 ccm |
| 3000 UXyl/100 kg flour | 1468 ccm |
| 4500 UXyl/100 kg flour | 1484 ccm |

Accordingly, the properties of the commercially available enzyme are not only reached but actually exceeded by the bacteria xylanases according to the invention.

Having now fully described the invention, it will be apparent to one of ordinary skill in the art that many changes and modifications can be made thereto without departing from the spirit or scope of the invention as set forth herein.

---

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 1413 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:1:

| | | | | | | |
|---|---|---|---|---|---|---|
| GGATCGTGAC | GGTCGGCTTG | TCCGTTCTCG | GTATCGTTCT | TTTCATTGTC | CTCATGACGC | 60 |
| TCGGCATCGT | GGACGACGCG | TTTAATAATA | TTGATGCCAA | TACATATTAA | AAAGGAAAAT | 120 |
| CCCGGCGCAT | CCGCCCGGGA | TTTTTTCTTA | TTCCGCTTCT | CCGACAACGG | TAAAGTTTTT | 180 |
| CTGCTTTGGA | TTTGCCAATA | CGGCGGCGAA | CAGCATTGAC | GTTGTATGCA | GATATTCTTT | 240 |
| CGACAAAAAA | GTTTTTTCAA | ATAAACGTT | TCCTCAGAGT | TTCAACTGAA | ATCACTCAGT | 300 |
| TCTGCGAAAT | AAAACTATGG | CGGTACAAGA | CCACTCATCA | TACAATTTTT | TGGGTCTTTG | 360 |
| TAATTAAATT | ACAATTGTTC | TTAATATTCA | CCCATGTATT | CATGCTATTA | TATTGAAAGG | 420 |
| AACGATCAAA | AGCGTTGGCG | TTCGTTAAAT | ATTTACGAGT | GCTGCCTCAT | GTCAAAGTCA | 480 |
| GAAAAAATAG | TATAGGAGGT | AACATATGTT | TAAGTTTAAA | AAGAAATTCT | TAGTGGGATT | 540 |
| AACGGCAGCT | TTCATGAGTA | TCAGCATGTT | TTCGGCAACC | GCCTCTGCAG | CTGGCACAGA | 600 |
| TTACTGGCAA | AATTGGACTG | ACGGGGGCGG | GACAGTAAAC | GCAGTCAATG | GCTCTGGCGG | 660 |
| AAATTACAGT | GTTAATTGGT | CTAATACCGG | GAATTTCGTT | GTTGGTAAAG | GCTGGACTAC | 720 |
| AGGCTCGCCA | TTTAGAACAA | TAAACTATAA | TGCCGGTGTT | TGGGCGCCGA | ATGGCAATGG | 780 |
| ATATTTGACT | TTATATGGCT | GGACGAGATC | GCCCCTCATC | GAATATTATG | TGGTGGATTC | 840 |
| ATGGGGTACT | TACAGACCTA | CCGGAACGTA | TAAAGGTACC | GTAAAGAGTG | ATGGAGGTAC | 900 |
| ATATGACATA | TATACAACGA | CACGTTATAA | CGCACCTTCC | ATTGATGGCG | ATAACACTAC | 960 |
| TTTTACGCAG | TACTGGAGTG | TCCGCCAGTC | GAAGAGACCG | ACCGGAAGCA | ACGCTGCAAT | 1020 |
| CACTTTCAGC | AATCATGTTA | ACGCATGGAA | GAGCCATGGA | ATGAATCTGG | GCAGTAATTG | 1080 |
| GGCTTATCAA | GTCTTAGCGA | CAGAAGGATA | TAAAAGCAGC | GGAAGTTCTA | ATGTAACAGT | 1140 |
| GTGGTAACAG | CTCATCTCTA | ATGAGGGGCA | GCTAACGGGC | TGCTGATCGT | TCCTTGAGAA | 1200 |
| ATTTTATAAT | GATTGTGAAG | AGGCGAACGG | TTTTGGCATT | ACCGGAGGCA | GGATATTCTC | 1260 |
| CATCAGTTTT | TTTAGCGCGT | ATTAAAATAA | GAGTTCCGTC | TTTTTTTGGT | AACCCGCTTA | 1320 |
| CAACAGACAC | CTTCACATAA | GCCTTAAGCA | AAATAAAAAT | ATCCCGGTTA | CCACCTCCTT | 1380 |
| TAGTTTCGGA | GGTTTTCTTC | ATTAAACAGA | TCC | | | 1413 |

( 2 ) INFORMATION FOR SEQ ID NO:2:

( i ) SEQUENCE CHARACTERISTICS:
( A ) LENGTH: 642 base pairs
( B ) TYPE: nucleic acid
( C ) STRANDEDNESS: unknown
( D ) TOPOLOGY: unknown ( i i ) MOLECULE TYPE: DNA (genomic)

( i x ) FEATURE:
      ( A ) NAME/KEY: CDS
      ( B ) LOCATION: 1..639

( x i ) SEQUENCE DESCRIPTION: SEQ ID NO:2:

| | | | | | | | | | | | | | | | | |
|---|---|---|---|---|---|---|---|---|---|---|---|---|---|---|---|---|
| ATG | TTT | AAG | TTT | AAA | AAG | AAA | TTC | TTA | GTG | GGA | TTA | ACG | GCA | GCT | TTC | 48 |
| Met | Phe | Lys | Phe | Lys | Lys | Lys | Phe | Leu | Val | Gly | Leu | Thr | Ala | Ala | Phe | |
| 1 | | | | 5 | | | | | 10 | | | | | 15 | | |
| ATG | AGT | ATC | AGC | ATG | TTT | TCG | GCA | ACC | GCC | TCT | GCA | GCT | GGC | ACA | GAT | 96 |
| Met | Ser | Ile | Ser | Met | Phe | Ser | Ala | Thr | Ala | Ser | Ala | Ala | Gly | Thr | Asp | |
| | | | 20 | | | | | 25 | | | | | 30 | | | |
| TAC | TGG | CAA | AAT | TGG | ACT | GAC | GGG | GGC | GGG | ACA | GTA | AAC | GCA | GTC | AAT | 144 |
| Tyr | Trp | Gln | Asn | Trp | Thr | Asp | Gly | Gly | Gly | Thr | Val | Asn | Ala | Val | Asn | |
| | | | 35 | | | | | 40 | | | | | 45 | | | |
| GGC | TCT | GGC | GGA | AAT | TAC | AGT | GTT | AAT | TGG | TCT | AAT | ACC | GGG | AAT | TTC | 192 |
| Gly | Ser | Gly | Gly | Asn | Tyr | Ser | Val | Asn | Trp | Ser | Asn | Thr | Gly | Asn | Phe | |
| | | 50 | | | | | 55 | | | | | 60 | | | | |
| GTT | GTT | GGT | AAA | GGC | TGG | ACT | ACA | GGC | TCG | CCA | TTT | AGA | ACA | ATA | AAC | 240 |
| Val | Val | Gly | Lys | Gly | Trp | Thr | Thr | Gly | Ser | Pro | Phe | Arg | Thr | Ile | Asn | |
| 65 | | | | | 70 | | | | | 75 | | | | | 80 | |
| TAT | AAT | GCC | GGT | GTT | TGG | GCG | CCG | AAT | GGC | AAT | GGA | TAT | TTG | ACT | TTA | 288 |
| Tyr | Asn | Ala | Gly | Val | Trp | Ala | Pro | Asn | Gly | Asn | Gly | Tyr | Leu | Thr | Leu | |
| | | | | 85 | | | | | 90 | | | | | 95 | | |
| TAT | GGC | TGG | ACG | AGA | TCG | CCC | CTC | ATC | GAA | TAT | TAT | GTG | GTG | GAT | TCA | 336 |
| Tyr | Gly | Trp | Thr | Arg | Ser | Pro | Leu | Ile | Glu | Tyr | Tyr | Val | Val | Asp | Ser | |
| | | | 100 | | | | | 105 | | | | | 110 | | | |
| TGG | GGT | ACT | TAC | AGA | CCT | ACC | GGA | ACG | TAT | AAA | GGT | ACC | GTA | AAG | AGT | 384 |
| Trp | Gly | Thr | Tyr | Arg | Pro | Thr | Gly | Thr | Tyr | Lys | Gly | Thr | Val | Lys | Ser | |
| | | 115 | | | | | 120 | | | | | 125 | | | | |
| GAT | GGA | GGT | ACA | TAT | GAC | ATA | TAT | ACA | ACG | ACA | CGT | TAT | AAC | GCA | CCT | 432 |
| Asp | Gly | Gly | Thr | Tyr | Asp | Ile | Tyr | Thr | Thr | Thr | Arg | Tyr | Asn | Ala | Pro | |
| | | 130 | | | | | 135 | | | | | 140 | | | | |
| TCC | ATT | GAT | GGC | GAT | AAC | ACT | ACT | TTT | ACG | CAG | TAC | TGG | AGT | GTC | CGC | 480 |
| Ser | Ile | Asp | Gly | Asp | Asn | Thr | Thr | Phe | Thr | Gln | Tyr | Trp | Ser | Val | Arg | |
| 145 | | | | | 150 | | | | | 155 | | | | | 160 | |
| CAG | TCG | AAG | AGA | CCG | ACC | GGA | AGC | AAC | GCT | GCA | ATC | ACT | TTC | AGC | AAT | 528 |
| Gln | Ser | Lys | Arg | Pro | Thr | Gly | Ser | Asn | Ala | Ala | Ile | Thr | Phe | Ser | Asn | |
| | | | | 165 | | | | | 170 | | | | | 175 | | |
| CAT | GTT | AAC | GCA | TGG | AAG | AGC | CAT | GGA | ATG | AAT | CTG | GGC | AGT | AAT | TGG | 576 |
| His | Val | Asn | Ala | Trp | Lys | Ser | His | Gly | Met | Asn | Leu | Gly | Ser | Asn | Trp | |
| | | | 180 | | | | | 185 | | | | | 190 | | | |
| GCT | TAT | CAA | GTC | TTA | GCG | ACA | GAA | GGA | TAT | AAA | AGC | AGC | GGA | AGT | TCT | 624 |
| Ala | Tyr | Gln | Val | Leu | Ala | Thr | Glu | Gly | Tyr | Lys | Ser | Ser | Gly | Ser | Ser | |
| | | | 195 | | | | | 200 | | | | | 205 | | | |
| AAT | GTA | ACA | GTG | TGG | TAA | | | | | | | | | | | 642 |
| Asn | Val | Thr | Val | Trp | | | | | | | | | | | | |
| | | 210 | | | | | | | | | | | | | | |

( 2 ) INFORMATION FOR SEQ ID NO:3:

( i ) SEQUENCE CHARACTERISTICS:
        ( A ) LENGTH: 213 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| | | | | | | | | | | | | | | | |
|---|---|---|---|---|---|---|---|---|---|---|---|---|---|---|---|
| Met | Phe | Lys | Phe | Lys | Lys | Lys | Phe | Leu | Val | Gly | Leu | Thr | Ala | Ala | Phe |
| 1 | | | | 5 | | | | | 10 | | | | | 15 | |
| Met | Ser | Ile | Ser | Met | Phe | Ser | Ala | Thr | Ala | Ser | Ala | Ala | Gly | Thr | Asp |
| | | | 20 | | | | | 25 | | | | | 30 | | |
| Tyr | Trp | Gln | Asn | Trp | Thr | Asp | Gly | Gly | Gly | Thr | Val | Asn | Ala | Val | Asn |
| | | | 35 | | | | | 40 | | | | | 45 | | |

-continued

| | | | | | | | | | | | | | |
|---|---|---|---|---|---|---|---|---|---|---|---|---|---|
| Gly | Ser<br>50 | Gly | Gly | Asn | Tyr | Ser<br>55 | Val | Asn | Trp | Ser | Asn<br>60 | Thr | Gly | Asn | Phe |
| Val<br>65 | Val | Gly | Lys | Gly | Trp<br>70 | Thr | Thr | Gly | Ser | Pro<br>75 | Phe | Arg | Thr | Ile | Asn<br>80 |
| Tyr | Asn | Ala | Gly | Val<br>85 | Trp | Ala | Pro | Asn | Gly<br>90 | Asn | Gly | Tyr | Leu | Thr<br>95 | Leu |
| Tyr | Gly | Trp | Thr<br>100 | Arg | Ser | Pro | Leu | Ile<br>105 | Glu | Tyr | Tyr | Val | Val<br>110 | Asp | Ser |
| Trp | Gly | Thr<br>115 | Tyr | Arg | Pro | Thr | Gly<br>120 | Thr | Tyr | Lys | Gly | Thr<br>125 | Val | Lys | Ser |
| Asp | Gly<br>130 | Gly | Thr | Tyr | Asp | Ile<br>135 | Tyr | Thr | Thr | Thr | Arg<br>140 | Tyr | Asn | Ala | Pro |
| Ser<br>145 | Ile | Asp | Gly | Asp | Asn<br>150 | Thr | Thr | Phe | Thr | Gln<br>155 | Tyr | Trp | Ser | Val | Arg<br>160 |
| Gln | Ser | Lys | Arg | Pro<br>165 | Thr | Gly | Ser | Asn | Ala<br>170 | Ala | Ile | Thr | Phe | Ser<br>175 | Asn |
| His | Val | Asn | Ala<br>180 | Trp | Lys | Ser | His | Gly<br>185 | Met | Asn | Leu | Gly | Ser<br>190 | Asn | Trp |
| Ala | Tyr | Gln<br>195 | Val | Leu | Ala | Thr | Glu<br>200 | Gly | Tyr | Lys | Ser | Ser<br>205 | Gly | Ser | Ser |
| Asn | Val | Thr<br>210 | Val | Trp | | | | | | | | | | | |

What is claimed as new and desired to be secured by Letters Patent of the United States is:

1. A bacterial xylanase having the amino acid sequence according to SEQ ID NO:3.

2. A bacterial xylanase produced by culturing *Bacillus subtilis* DSM 7147.

3. A baking agent for the production of bread and baked goods which comprises a baking emulsifier and a xylanase having the amino acid sequence shown in SEQ ID NO:3.

* * * * *